United States Patent
Knighton et al.

(10) Patent No.: US 9,005,449 B2
(45) Date of Patent: Apr. 14, 2015

(54) USE OF MOSS TO REDUCE DISINFECTION BY-PRODUCTS IN WATER TREATED WITH DISINFECTANTS

(75) Inventors: David R. Knighton, Minneapolis, MN (US); Vance D. Fiegel, Shakopee, MN (US)

(73) Assignee: Embro Corporation, St. Louis Park, MN (US)

(*) Notice: Subject to any disclaimer, the term of this patent is extended or adjusted under 35 U.S.C. 154(b) by 223 days.

(21) Appl. No.: 13/605,377

(22) Filed: Sep. 6, 2012

(65) Prior Publication Data

US 2013/0140239 A1 Jun. 6, 2013

Related U.S. Application Data (60) Provisional application No. 61/531,952, filed on Sep. 7, 2011.

(51) Int. Cl.
C02F 1/28 (2006.01)
C02F 1/76 (2006.01)
(Continued)

(52) U.S. Cl.
CPC . *C02F 1/286* (2013.01); *C02F 1/76* (2013.01); *C02F 2101/12* (2013.01); *C02F 2101/36* (2013.01); *C02F 2103/42* (2013.01); *C02F 2209/001* (2013.01); *C02F 2209/003* (2013.01); *C02F 2209/29* (2013.01); *C02F 2303/185* (2013.01); *B01J 2220/485* (2013.01)

(58) Field of Classification Search
CPC .. C02F 1/286; C02F 2101/36; C02F 2103/42; C02F 2303/185

USPC .......................................................... 210/691
See application file for complete search history.

(56) References Cited

U.S. PATENT DOCUMENTS 221,909 A 3/1879 Collins
239,564 A 3/1881 Smith
(Continued)

FOREIGN PATENT DOCUMENTS

DE 103 52 460 A1 6/2005
GB 2 134 791 A 8/1984
(Continued)

OTHER PUBLICATIONS

English Language Translation of SU 810612 A2 (Lebedev et al) completed by the USPTO on Aug. 2014, No. PTO 14/5493, nine pages.*

(Continued)

*Primary Examiner* — Matthew O Savage
(74) *Attorney, Agent, or Firm* — Popovich, Wiles & O'Connell, P.A.

(57) ABSTRACT

A method of reducing disinfection by-products in water treated with disinfectants including contacting the water with an amount of a non-decomposed moss effective to reduce the level of disinfection by-products. A method of determining the effectiveness of a first method of reducing disinfection by-products in water treated with disinfectants, the first method including contacting the water with an amount of a non-decomposed moss effective to reduce the level of disinfection by-products, the method including determining the effectiveness of the first method by measuring the level of the disinfection by-products in water treated with disinfectants and contacted with the amount of non-decomposed moss.

27 Claims, 3 Drawing Sheets

(51) Int. Cl.
  *C02F 101/12* (2006.01)
  *C02F 101/36* (2006.01)
  *C02F 103/42* (2006.01)

(56) References Cited

U.S. PATENT DOCUMENTS

| | | | |
|---|---|---|---|
| 413,621 A | 8/1889 | Glaister |
| 1,914,824 A | 6/1933 | Eberhard |
| 2,605,589 A | 8/1952 | Kuestner |
| 2,785,106 A | 3/1957 | Mendelsohn |
| 2,876,588 A | 3/1959 | Tietz et al. |
| 3,635,816 A | 1/1972 | Golub |
| 3,835,042 A | 9/1974 | Lalancette et al. |
| 3,890,910 A | 6/1975 | Angruner |
| 3,894,355 A | 7/1975 | Carothers |
| 3,903,267 A | 9/1975 | Miler et al. |
| 3,914,901 A | 10/1975 | Muldner |
| 3,961,444 A | 6/1976 | Skaife |
| 4,002,566 A | 1/1977 | Smith |
| 4,014,676 A | 3/1977 | Carter et al. |
| 4,079,543 A | 3/1978 | Stoller |
| 4,123,359 A | 10/1978 | Smith |
| 4,146,646 A | 3/1979 | Percival et al. |
| 4,190,981 A | 3/1980 | Muldner |
| 4,215,692 A | 8/1980 | Levesque |
| 4,272,527 A | 6/1981 | Belkevich et al. |
| 4,272,962 A | 6/1981 | Viscovich et al. |
| 4,402,941 A | 9/1983 | Vaillancourt |
| 4,528,774 A | 7/1985 | Skaife |
| 4,537,590 A | 8/1985 | Pieniak |
| 4,551,165 A | 11/1985 | Warner |
| 4,560,372 A | 12/1985 | Pieniak |
| 4,588,400 A | 5/1986 | Ring et al. |
| 4,588,693 A | 5/1986 | Strobel |
| 4,618,496 A | 10/1986 | Brasseur |
| 4,624,790 A | 11/1986 | Kamperman et al. |
| 4,676,196 A | 6/1987 | Lojek et al. |
| 4,704,818 A | 11/1987 | Cameron |
| 4,788,146 A | 11/1988 | Ring et al. |
| 4,798,723 A | 1/1989 | Dart et al. |
| 4,827,871 A | 5/1989 | Morrison |
| 4,861,481 A | 8/1989 | Allen, III |
| 4,936,910 A | 6/1990 | Dadgar et al. |
| 4,941,282 A | 7/1990 | Milstein |
| 4,971,702 A | 11/1990 | Renk |
| 4,999,202 A | 3/1991 | Cronje et al. |
| 5,049,002 A | 9/1991 | Cole |
| 5,049,265 A | 9/1991 | Boyd et al. |
| 5,060,598 A | 10/1991 | Richards |
| 5,108,614 A | 4/1992 | Ross et al. |
| 5,118,504 A | 6/1992 | Clement et al. |
| 5,178,769 A | 1/1993 | Simpson et al. |
| 5,181,802 A | 1/1993 | Thengs et al. |
| 5,187,200 A | 2/1993 | Rainer |
| 5,242,582 A | 9/1993 | Marioni |
| 5,271,987 A | 12/1993 | Iskra |
| 5,290,554 A | 3/1994 | Tolpa et al. |
| 5,296,293 A | 3/1994 | Jobst |
| 5,346,514 A | 9/1994 | Molnar et al. |
| 5,360,117 A | 11/1994 | Tolpa et al. |
| 5,360,608 A | 11/1994 | Harman et al. |
| 5,373,025 A | 12/1994 | Gay |
| 5,378,460 A | 1/1995 | Zuckerman et al. |
| 5,389,257 A | 2/1995 | Todd et al. |
| 5,403,584 A | 4/1995 | Crawford et al. |
| 5,418,165 A | 5/1995 | McBeath |
| 5,454,191 A | 10/1995 | Mayeda et al. |
| 5,476,523 A | 12/1995 | Hiraoka |
| 5,476,591 A | 12/1995 | Green |
| 5,478,463 A | 12/1995 | Brownawell et al. |
| 5,527,526 A | 6/1996 | Crawford |
| 5,533,300 A | 7/1996 | Kesler |
| 5,543,300 A | 8/1996 | Inglot et al. |
| 5,549,889 A | 8/1996 | Zuckerman et al. |
| 5,580,192 A | 12/1996 | Ogawa et al. |
| 5,584,140 A | 12/1996 | Byrne |
| 5,597,489 A | 1/1997 | Schneider et al. |
| 5,602,071 A | 2/1997 | Summers et al. |
| 5,608,989 A | 3/1997 | Behrens |
| 5,635,029 A | 6/1997 | Levesque et al. |
| 5,688,259 A | 11/1997 | Osborn, III et al. |
| 5,690,827 A | 11/1997 | Simmering et al. |
| 5,693,220 A | 12/1997 | Sceusa |
| 5,704,989 A | 1/1998 | Page |
| 5,707,527 A | 1/1998 | Knutson et al. |
| 5,718,697 A | 2/1998 | Chauvette et al. |
| 5,747,050 A | 5/1998 | Tolpa et al. |
| 5,759,225 A | 6/1998 | Tanoshima |
| 5,797,894 A | 8/1998 | Cadieux et al. |
| 5,807,484 A | 9/1998 | Couture et al. |
| 5,814,233 A | 9/1998 | Starkey et al. |
| 5,829,193 A | 11/1998 | Otake et al. |
| 5,843,415 A | 12/1998 | Klar |
| 5,853,460 A | 12/1998 | Alcordo |
| 5,853,706 A | 12/1998 | Klar |
| 5,895,380 A | 4/1999 | Turi et al. |
| 5,934,011 A | 8/1999 | Ishioka et al. |
| 5,942,478 A | 8/1999 | Lopes |
| 5,945,446 A | 8/1999 | Laub |
| 5,980,748 A | 11/1999 | Auger et al. |
| 5,997,812 A | 12/1999 | Burnham et al. |
| 6,012,251 A | 1/2000 | Siegert |
| 6,027,639 A | 2/2000 | Lenhart, Jr. et al. |
| 6,030,533 A | 2/2000 | Karamanev et al. |
| 6,036,851 A | 3/2000 | Simmering et al. |
| 6,040,032 A | 3/2000 | Isräel et al. |
| 6,042,743 A | 3/2000 | Clemenson |
| 6,048,131 A | 4/2000 | Laak |
| 6,062,220 A | 5/2000 | Whitaker et al. |
| 6,062,229 A | 5/2000 | Kandratavich et al. |
| 6,074,988 A | 6/2000 | King et al. |
| 6,096,266 A | 8/2000 | Duroselle |
| 6,100,081 A | 8/2000 | Buelna |
| 6,100,382 A | 8/2000 | Wolfe et al. |
| 6,123,036 A | 9/2000 | Decker |
| 6,132,599 A | 10/2000 | Chaffee |
| 6,187,183 B1 | 2/2001 | Weaver et al. |
| 6,190,548 B1 | 2/2001 | Frick |
| 6,197,081 B1 | 3/2001 | Schmidt |
| 6,200,469 B1 | 3/2001 | Wallace |
| 6,205,708 B1 | 3/2001 | Gatliff |
| 6,217,780 B1 | 4/2001 | Denkewicz, Jr. et al. |
| 6,242,230 B1 | 6/2001 | Batich et al. |
| 6,255,117 B1 | 7/2001 | Johnson |
| 6,264,841 B1 | 7/2001 | Tudor |
| 6,267,962 B1 | 7/2001 | Hart et al. |
| 6,271,020 B1 | 8/2001 | Coleman |
| 6,276,300 B1 | 8/2001 | Lewis, II et al. |
| 6,293,045 B1 | 9/2001 | Morgan |
| 6,319,405 B1 | 11/2001 | Roy et al. |
| 6,322,699 B1 | 11/2001 | Fernandez |
| 6,336,291 B1 | 1/2002 | Skuba |
| 6,337,025 B1 | 1/2002 | Clemenson |
| 6,337,203 B1 | 1/2002 | Beaulieu |
| 6,352,644 B1 | 3/2002 | Hawthorne et al. |
| 6,365,214 B1 | 4/2002 | Kirk |
| 6,365,384 B1 | 4/2002 | Iijima |
| 6,372,128 B1 | 4/2002 | Belhumeur |
| 6,378,244 B1 | 4/2002 | Iwata et al. |
| 6,403,366 B1 | 6/2002 | Kim |
| 6,406,627 B1 | 6/2002 | Wallace |
| 6,406,690 B1 | 6/2002 | Peleg et al. |
| 6,555,007 B1 * | 4/2003 | Bilkey .................. 210/673 |
| 6,620,321 B2 | 9/2003 | Festa et al. |
| 6,638,959 B2 | 10/2003 | Howarth et al. |
| 6,749,748 B1 | 6/2004 | Macpherson et al. |
| 6,815,050 B2 * | 11/2004 | Rainer .................. 428/317.9 |
| 6,890,651 B2 * | 5/2005 | Bilkey .................. 428/402 |
| 7,497,947 B2 | 3/2009 | Knighton et al. |
| 7,625,486 B2 | 12/2009 | Knighton et al. |
| 7,625,489 B2 | 12/2009 | Knighton et al. |
| 2001/0007065 A1 | 7/2001 | Blanchard et al. |
| 2001/0016721 A1 | 8/2001 | Salerno et al. |
| 2001/0025162 A1 | 9/2001 | Roe et al. |

(56) References Cited

U.S. PATENT DOCUMENTS

| | | | |
|---|---|---|---|
| 2001/0027304 | A1 | 10/2001 | Mayer |
| 2002/0134728 | A1 | 9/2002 | Festa et al. |
| 2002/0139742 | A1 | 10/2002 | Svirklys et al. |
| 2004/0031193 | A1 | 2/2004 | Anderson |
| 2004/0112811 | A1 | 6/2004 | Lindemulder |
| 2006/0032123 | A1 | 2/2006 | Knighton et al. |
| 2006/0032124 | A1 | 2/2006 | Knighton et al. |
| 2006/0231451 | A1 | 10/2006 | Takeda et al. |
| 2009/0120871 | A1 | 5/2009 | Knighton et al. |
| 2009/0152185 | A1 | 6/2009 | Knighton et al. |
| 2010/0320144 | A1 | 12/2010 | Knighton et al. |
| 2011/0094949 | A1* | 4/2011 | Just .................... 210/85 |
| 2011/0132835 | A1 | 6/2011 | Knighton et al. |
| 2011/0163027 | A1 | 7/2011 | Knighton et al. |
| 2011/0290720 | A1 | 12/2011 | Knighton et al. |
| 2012/0125838 | A1 | 5/2012 | Knighton et al. |
| 2012/0152828 | A1 | 6/2012 | Fiegel et al. |

FOREIGN PATENT DOCUMENTS

| | | |
|---|---|---|
| GB | 2 134 793 A | 8/1984 |
| JP | 8-1188 A | 1/1996 |
| JP | 11-56096 A | 3/1999 |
| JP | 2001-62478 A | 3/2001 |
| JP | 2001-226991 A | 8/2001 |
| JP | 2002-360060 A | 12/2002 |
| KR | 20030053231 A | 6/2003 |
| SU | 810612 A1 | 3/1981 |
| WO | WO 97/07883 A1 | 3/1997 |
| WO | WO 2004/060049 A1 | 7/2004 |
| WO | WO 2005/081641 A2 | 9/2005 |
| WO | WO 2005/102935 A2 | 11/2005 |
| WO | WO 2006/109078 A1 | 10/2006 |
| WO | WO 2007/077459 A2 | 7/2007 |

OTHER PUBLICATIONS

Abstract for JP 8-1188 (1996) (1 page).
Abstract for JP 11-56096 (1999) (1 page).
Abstract for JP 2001-62478 (2001) (1 page).
Abstract for JP 2001-226991 A (2001) (1 page).
Abstract for JP 2002-360060 (2002) (1 page).
Abstract for KR20030053231A (2003) (1 page).
Abstract for WO 2004/060049 A1 (2004) (1 page).
Abstract for WO 2005/081641 A2 (2005) (1 page).
Asakawa, "Biologically Active Substances Obtained From Bryophytes1.2", Journ. Hattori Bot. Lab. No. 50:123-142 (Sep. 1981).
Azegami et al., Effect of Iron Limitation on "*Pseudomonas plantarii*" Growth and Tropolone and Protein Production, AEM, 54(3):844-847 (Mar. 1988).
Banerjee et al., "Antibiotic Activity of Bryophytes1", The Bryologist, 82(2):141-153 (1979).
Borel et al., "Dicranin, an Antimicrobial and 15-Lipoxygenase Inhibitor From the Moss *Dicranum scoparium*", Journal of Natural Products, 56(7):1071-1077 (Jul. 1993).
*Sphagnum papillosum*-Lindberg[online]. Science Museum of Minnesota 2004-2005[retrieved on Dec. 2, 2009]. Retrieved from the Internet: <URL: http://www.sciencebuzz.org/museum/object/2000_12_sphagnum_papillosum_lindberg> (1 page).
Abstract for DE 103 52 460 A1 (2 pages), (2005).
Machine Translation of DE 103 52 460 A1 (9 pages), (2005).
International Search Report and Written Opinion of PCT Application No. PCT/US2012/053906, dated Nov. 30, 2012 (12 pages).
Diouf et al., Influence of Tropolone on Poria placenta Wood Degradation, AEM, 68(9):4377-4382 (Sep. 2002), HTTP://aem.asm.org/cgi/content/full/68/9/4377.
Gstoettner et al., "Accumulation of Cadmium, Chromium, and Zinc by the Moss *Sphagnum papillosum* Lindle", Water, Air, and Soil Pollution, 93:321-330 (1997).
International Search Report for PCT Application No. PCT/US2005/012915, Jul. 26, 2005 (12 pages).
"Iron Chelator Prevents Bacterial Biofilm Formation", http://pubs.acs.org/cen, C & EN, Jun. 3, 2002, p. 31.
Jones et al., "A Preliminary Study of Antimicrobial Activity in Some Malaysian Mosses (Bryophytina)", Malays. Appl. Biol., 12(1):5-13 (1983).
Latiff et al., "The Effect of Moss Extracts on the Growth of Three Species of Bacteria", Malays. Appl. Biol., 18(1):77-84 (1989).
Martins et al., "Cadmium(II) and Zinc(II) Adsorption by the Aquatic Moss *Fontinalis antipyretica*: Effect of Temperature pH and Water Hardness," Water Research, 38:693-699 (2004).
McCleary et al., "Mosses and Antibiosis", pp. 309-314 (date unknown).
Painter et al., "The Cation-Exchanger of *Sphagnum* Mosses: an Unusual Form of Holocellulose", Carbohydrate Research, 66:C1-C3 (1978).
Podterob et al., "A History of the Medicinal Use of Plants of the Genus *Sphagnum*," Pharmaceutical Chemistry Journal, 36(4):192-194 (2002).
Smidsrød et al., "Contribution of Carbohydrates to the Catio-Exchange Selectivity of Aquatic Humus From Peat-Bog Water", Carbohydrate Research, 127:267-281 (1984).
*Sphagnum papillosum*—Lindberg[online]. Science Museum of Minnesota 2004-2005[retrieved on Dec. 2, 2009]. Retrieved from the Internet: <URL: http://www.sciencebuzz.org/museum/object/2000_12_sphagnum_papillosum_lindberg> (1 page).
Translation of the Jun. 6, 2008 First Office Action in Chinese Application No. 200580011538.1, filed Oct. 12, 2006 (7 pages).
Verhoeven et al., "The Ecological Significance of Organochemical Compounds in *Sphagnum*," Acta Bot. Neerl., 46 (2):117-130 (Jun. 1997).
"*Sphagnum cristatum*" published in 2002 at http://www.anbg.gov.au/gnp/interns-2002/sphagnum-cristatum.html.
New World Encyclopedia. *Sphagnum* [online], [retrieved on Mar. 11, 2011]. Retrieved from the Internet <URL:http://www.newworldencyclopedia.org/entry/Sphagnum>.
Børsheim et al., "Preservation of Fish by Embedment in *Sphagnum* Moss, Peat or Holocellulose: Experimental Proof of the Oxopolysaccharidic Nature of the Preservative Substance and of its Antimicrobial and Tanning Action", ScienceDirect—Innovative Food Science & Emerging Technologies, vol. 2, Issue 1, Mar. 2001, pp. 63-74.
Van Hoof et al., Antimicrobial and Antiviral Screening of Byryophyta, pp. 223-229 (date unknown).
Abstract for WO 2004/060049 A1 (1 page).
Jan. 25, 2012 Notification of Transmittal of the International Search Report and the Written Opinion of the International Searching Authority, or the Declaration for International Application No. PCT/US2011/049697 (10 pages).

\* cited by examiner

USE OF MOSS TO REDUCE DISINFECTION BY-PRODUCTS IN WATER TREATED WITH DISINFECTANTS

This application claims the benefit of U.S. Provisional Application No. 61/531,952, filed Sep. 7, 2011, entitled "Use of Moss to Reduce Disinfection By-Products in Water Treated With Disinfectants", the contents of which are hereby incorporated by reference.

FIELD OF THE INVENTION

This invention relates to methods of reducing disinfection by-products in water treated with disinfectants.

BACKGROUND OF THE INVENTION

Disinfection by-products (DBP) are created in pool systems through the chemical reaction of the disinfectant, which is usually a chlorine disinfectant, with the organic matter contained within the water and on the surfaces of the pool or spa system. Many of the DBP's created are toxic compounds such as trihalomethanes (THM) and haloacetic acids. The trihalomethanes are chloroform ($CHCl_3$), bromoform ($CHBr_3$), dichlorobromomethane ($CHCl_2Br$), and dibromochloromethane ($CHBr_2Cl$). The DBP's are what cause the odor and health issues associated with pool facilities and pool use.

Chlorine based disinfectants include chlorine gas ($Cl_2$), sodium or calcium hypochlorite (NaOCl or $Ca[OCl]_2$), chlorinated isocyanurates (e.g., sodium dichloro-s-triazinetrione dihydrate), bromochlorodimethylhydantoin ($C_5H_6BrClN_2O_2$), and chlorine dioxide ($ClO_2$). Disinfection by-products are described in papers by Lakind et al., *Environ. Sci. Technol.*, 44:3205-3210 (2010) and Richardson et al., *Environmental Health Perspectives*, 118(11):1523-1530 (2010), both of which are hereby incorporated by reference herein.

Previous studies have demonstrated that sphagnum moss significantly inhibits the growth of free-floating (planktonic) bacteria. See U.S. Pat. No. 7,497,947 B2 and U.S. Patent Application Publication No. 2006/0032124 A1, both of which are incorporated by reference herein. Other studies have demonstrated that sphagnum moss inhibits and removes biofilm. See U.S. Patent Application Publication No. 2012/0152828 A1. "Sphagnum moss" is a generic expression that designates a range of botanical species that co-exist in a sphagnous bog. It should be noted that "peat moss" refers generally to a decomposed or composted sphagnum moss. Sphagnum moss is commonly harvested for use in various products. The petals, and not the stems, of the moss preferably may be harvested. Typically large pieces of plant material (roots, twigs, etc.) are removed. Excess water is removed and the moss is air dried. The moss may be compressed prior to packaging or shipment. Various additives may be used to alter the absorption characteristics or mechanical properties of the moss. Because sphagnum moss is readily available and relatively inexpensive, it has been used in a variety of products, primarily for the absorption of fluids.

There is need in the art for a method of reducing disinfection by-products in water treated with disinfectants.

SUMMARY OF THE INVENTION

The invention provides a method of reducing disinfection by-products in water treated with disinfectants comprising contacting the water with an amount of a non-decomposed moss effective to reduce the level of disinfection by-products.

The invention provides a method of determining the effectiveness of a first method of reducing disinfection by-products in water treated with disinfectants, the first method comprising contacting the water with an amount of a non-decomposed moss effective to reduce the level of disinfection by-products, the method comprising determining the effectiveness of the first method by measuring the level of the disinfection by-products in water treated with disinfectants and contacted with the amount of non-decomposed moss.

The invention provides a method of determining the effectiveness of a first method of reducing disinfection by-products in water treated with disinfectants, the first method comprising contacting the water with an amount of a non-decomposed moss effective to reduce the level of disinfection by-products, the method comprising determining the effectiveness of the first method by measuring the level of the disinfection by-products in the air above the water treated with disinfectants and contacted with the amount of non-decomposed moss.

It is to be understood that both the foregoing general description and the following detailed description are exemplary and explanatory and are intended to provide further explanation of the invention as claimed.

DETAILED DESCRIPTION OF THE PREFERRED EMBODIMENTS

The invention provides a method of reducing disinfection by-products in water treated with disinfectants comprising contacting the water with an amount of a non-decomposed moss effective to reduce the level of disinfection by-products. In an embodiment, the water has been treated with a disinfectant selected from the group consisting of chlorinated, brominated, or other halogen containing disinfectants. In an embodiment, the disinfectant is a disinfectant that includes chlorine. In an embodiment, the non-decomposed moss is in the form of leaves or parts of leaves. In another embodiment, the non-decomposed moss is in the form of compressed leaves or parts of leaves.

In an embodiment, the non-decomposed moss is placed in a carrier. In an embodiment, the carrier is a mesh bag. In an embodiment, the non-decomposed moss is placed in a contact chamber. In an embodiment, the non-decomposed moss is placed in a filter cartridge. In an embodiment, the non-decomposed moss is placed in a surge tank of a pool. In one embodiment, the water is water in a spa, swimming pool, or splash deck.

In an embodiment, the level of disinfection by-products in the water is reduced by 20 percent or more after eight weeks. In another embodiment, the level of disinfection by-products in the water is reduced by 40 percent or more after eight weeks. In an embodiment, the level of disinfection by-products in the water is reduced by 60 percent or more after eight weeks. In an embodiment, the disinfection by-products whose level is reduced comprise trihalomethanes. In an embodiment, the disinfection by-products whose level is reduced comprise haloacetic acids. In an embodiment, the disinfection by-products whose level is reduced comprise chloroform.

In an embodiment, the disinfection by-products whose level is reduced comprise one or more of chloroform, bromoform, dichlorobromomethane, dibromochloromethane, 1,1,1-trichloro-2-propanone, 1,1,1-trichloroacetonitrile, chloral hydrate, dibromochloroacetic acid, dichlorobromoacetic acid, tribromoacetic acid, and trichloroacetic acid. In one embodiment, the disinfection by-products whose level is reduced comprise one or more of chloroform, bromoform, dichlorobromomethane, and dibromochloromethane.

In an embodiment, the disinfection by-products whose level is reduced consist of the group of chloroform, bromoform, dichlorobromomethane, dibromochloromethane, 1,1,1-trichloro-2-propanone, 1,1,1-trichloroacetonitrile, chloral hydrate, dibromochloroacetic acid, dichlorobromoacetic acid, tribromoacetic acid, and trichloroacetic acid. In one embodiment, the disinfection by-products whose level is reduced consist of the group of chloroform, bromoform, dichlorobromomethane, and dibromochloromethane.

In an embodiment, the non-decomposed moss is selected from the group consisting of *sphagnum papillosum*, *sphagnum cristatum*, and mixtures thereof.

In an embodiment, the level of disinfection by-products is reduced in the air above the water. In an embodiment, the disinfection by-products whose level is reduced in the air above the water comprise one or more of chloroform, bromoform, dichlorobromomethane, and dibromochloromethane. In one embodiment, the disinfection by-product whose level is reduced in the air above the water is chloroform. In an embodiment, the level of disinfection by-products in the air above the water is reduced by 20 percent or more after 28 weeks. In an embodiment, the level of disinfection by-products in the air above the water is reduced by 40 percent or more after 28 weeks.

The invention provides a method of determining the effectiveness of a first method of reducing disinfection by-products in water treated with disinfectants, the first method comprising contacting the water with an amount of a non-decomposed moss effective to reduce the level of disinfection by-products, the method comprising determining the effectiveness of the first method by measuring the level of the disinfection by-products in water treated with disinfectants and contacted with the amount of non-decomposed moss. In one embodiment, the level of disinfection by-products is measured in the water before and after treating the water with the non-decomposed moss. In an embodiment, the level of disinfection by-products is measured in the water at a first time and at a second time.

In one embodiment, the disinfection by-products whose level is measured comprise one or more of chloroform, bromoform, dichlorobromomethane, dibromochloromethane, 1,1,1-trichloro-2-propanone, 1,1,1-trichloroacetonitrile, chloral hydrate, dibromochloroacetic acid, dichlorobromoacetic acid, tribromoacetic acid, and trichloroacetic acid. In an embodiment, the disinfection by-products whose level is measured comprise one or more of chloroform, bromoform, dichlorobromomethane, and dibromochloromethane. In one embodiment, the disinfection by-products whose level is measured consist of the group of chloroform, bromoform, dichlorobromomethane, dibromochloromethane, 1,1,1-trichloro-2-propanone, 1,1,1-trichloroacetonitrile, chloral hydrate, dibromochloroacetic acid, dichlorobromoacetic acid, tribromoacetic acid, and trichloroacetic acid. In an embodiment, the disinfection by-products whose level is measured consist of the group of chloroform, bromoform, dichlorobromomethane, and dibromochloromethane.

The invention provides a method of determining the effectiveness of a first method of reducing disinfection by-products in water treated with disinfectants, the first method comprising contacting the water with an amount of a non-decomposed moss effective to reduce the level of disinfection by-products, the method comprising determining the effectiveness of the first method by measuring the level of the disinfection by-products in the air above the water treated with disinfectants and contacted with the amount of non-decomposed moss. In an embodiment, the level of disinfection by-products is measured in the air above the water before and after treating the water with the non-decomposed moss. In one embodiment, the level of disinfection by-products is measured in the air above the water at a first time and at a second time. In an embodiment, the disinfection by-products whose level is measured is chloroform.

In preferred embodiments, the moss is enclosed or encapsulated in a mesh material that prevents the moss from disintegrating in an aqueous environment. Preferred mesh materials include those comprising polymers such as nylon or polypropylene, with mesh sizes ranging from about 0.1 to 1 mm. Polymers are generally preferred because they are inexpensive and may be resistant to degradation.

Suitable for use in this invention are *S. papillosum*, which can be harvested from bogs in northern Minnesota, U.S.A., and *S. cristatum*, which is commercially available as a compressed board from Coastpak Holdings, Ltd., Hokitika, New Zealand. These species of moss can be used by themselves or together in the devices and systems of this invention. Typically and preferably the moss is cleaned to remove small particles, such as dirt, and larger debris, such as roots and leaves. Commercially available moss may be fumigated before it is packaged by a manufacturer in order to destroy seeds.

In a preferred embodiment, the moss is cut by mechanical means into a desired size and shape. The moss preferably is then sterilized by autoclaving, exposure to ethylene oxide, or by other means known to one of skill in the art. Sterilization destroys living organisms in the moss and thus avoids any problems of undesirable or foreign bacteria being introduced into the environment where a device of this invention is used. The moss is then ready for use. A carrier can be a polymer matrix, a biomatrix, membrane, gel, hydrogel, or mesh bag.

The moss can be compressed and can be in the form of strips or bricks. The moss can be sterilized by autoclaving, sterilized by chemical treatment, or sterilized by treatment with ethylene oxide. The moss can be washed with an acidic solution, especially a solution of acetic acid. The moss can be washed with an acidic solution and then washed with a salt solution.

The moss can be prepared by (i) drying non-decomposed moss; and (ii) sterilizing the moss. The method can further comprising compressing the moss, compressing the moss and cutting the moss into strips, sterilizing the moss by autoclaving, chemical treatment, or treatment with ethylene oxide. The moss can be sphagnum moss. The moss can be selected from the group consisting of *sphagnum papillosum*, *sphagnum cristatum*, and mixtures thereof.

The moss can be prepared by (i) contacting non-decomposed moss with an acidic solution; and (ii) drying the moss. The method can comprise contacting the non-decomposed moss with a salt solution after step (i). In one embodiment, the acidic solution is a solution of acetic acid. The moss can be sphagnum moss. The moss can be selected from the group consisting of *sphagnum papillosum, sphagnum cristatum*, and mixtures thereof.

Examples

A study was performed to document the levels of disinfection by-products (DPB) in an indoor pool facility and to monitor the ability of the sphagnum moss system to reduce DBP levels in the pool water and air. As noted above, disinfection by-products are created in pool systems through the chemical reaction of the chlorine disinfectant with the organic matter contained within the water of the pool or spa. Many of the DBP's created are toxic compounds such as trihalomethanes (THM) and haloacetic acids. These DBP's are what cause the odor and health issues associated with pool facilities and pool use.

Figure 1:
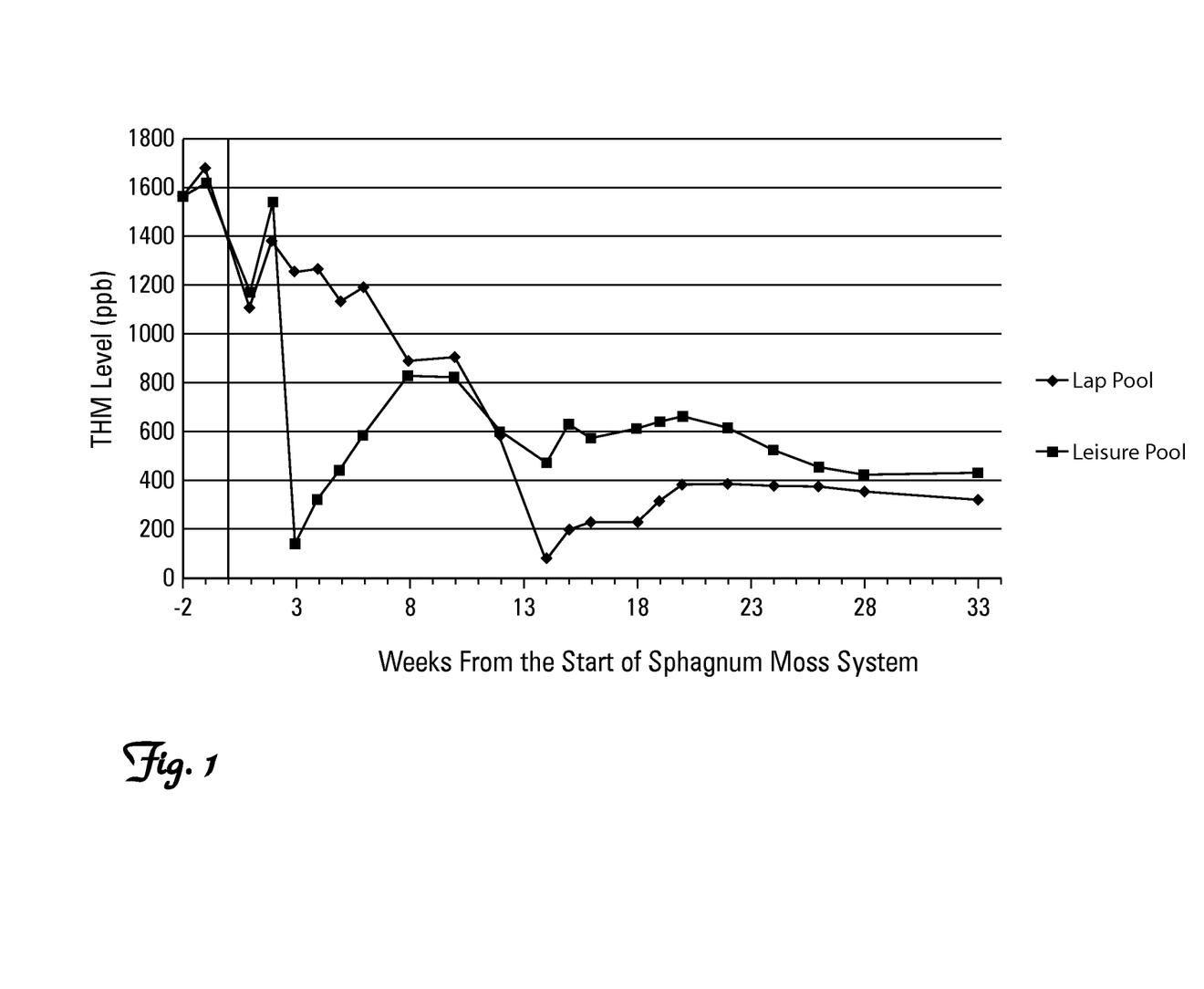
FIG. 1 shows the effects of the sphagnum moss system on THM levels in the water of the lap pool and leisure pool.

The study undertaken measured THM in the water of two swimming pools, a lap pool and a leisure pool, as well as the measurement of volatile organic compounds (VOC) in the air of the facility. At one and two weeks prior to the addition of the sphagnum moss system, baseline values of THM in the water of both pools were determined. In addition, air samples were taken at three locations throughout the pool area for the determination of VOC. As shown in FIG. 1, the baseline values of THM in each pool were approximately 1,600 ppb. Measurement of VOC demonstrated significant levels of chloroform in the air of 0.15 mg/m$^3$. Chloroform was present at relatively high levels while other VOC's were only present at very low levels. Chloroform is a volatile DBP that moves from the water phase, where it is created, into the air. It is also a THM, with known toxic properties and can be absorbed through the skin while in the water phase.

At week zero (the solid vertical line in FIG. 1) the sphagnum moss system was turned on. Following the installation and start-up of the sphagnum moss system, THM levels were monitored periodically for 33 weeks. Each pool, at some point in the study, had to be drained and refilled for operational reasons unrelated to the sphagnum moss system. This occurred just prior to week 3 in the leisure pool and to week 14 in the lap pool. As can be seen in FIG. 1, THM levels in the lap pool decreased continuously for the first 12 weeks. Following the refilling of each pool, THM levels rose from near zero to an intermediate level and then began to decrease again. At week 33 the THM levels appeared to be stabilizing at approximately 300 ppb for the lap pool and 400 ppb for the leisure pool. These values represent an 80% and 73%, respectively, reduction in THM levels from the starting point prior to the addition of the sphagnum moss system.

Due to the expense of the VOC testing, additional measurements have only been made at week 28. The baseline measurements of chloroform at the three locations were measured at one and two weeks prior to the initiation of the sphagnum moss treatment and were, on average, 0.15 mg/m$^3$ (Std. Dev. 0.020, n=6, range 0.12-0.18). The results from the testing at 28 weeks after the addition of the sphagnum moss system were, on average, 0.067 mg/m$^3$ (Std. Dev. 0.008; n=3, range 0.058-0.074; p<0.001 vs baseline values). This represents a 55% reduction in chloroform levels in the air of the pool facility.

These tests clearly demonstrate that the sphagnum moss system is effective at significantly reducing THM levels in the water of swimming pools. The data to date also demonstrate the ability of the sphagnum moss system to reduce volatile, toxic THM in the air of the facility. The reduction of these toxic DBP's in the water and the air of the pool facility will benefit the users of the pool facility and enhance the swimming member experience.

Figure 2:
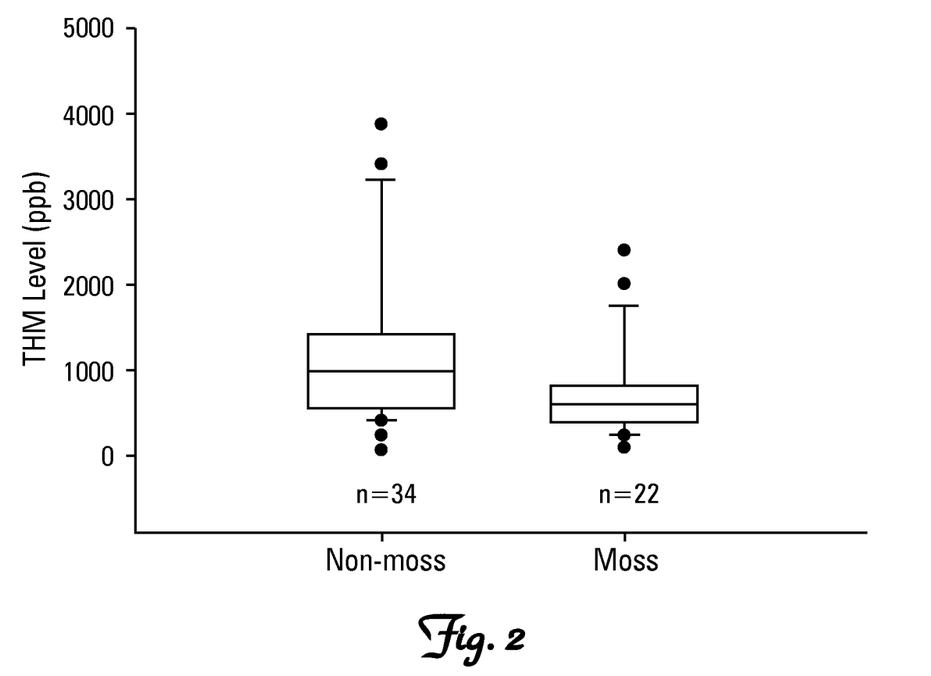
FIG. 2 shows the effects of the sphagnum moss system on THM levels in several swimming pools.

FIG. 2 is a box plot analysis of the THM data obtained from 34 control (non-moss treated) swimming pools and 22 moss-treated swimming pools (treated for a minimum of 2 months). The water in the moss-treated swimming pools was contacted with moss as described in the Materials and Methods for the leisure pool. However, the amount of moss varied from 6.5 grams/1000 gallons to 13 grams/1000 gallons based on pool temperature and the number of people using the pool. Water samples were collected and analyzed for THM levels as described in the Materials and Methods. The box plots depict the mean, the median, the 25th percentile-75th percentile (boxed area), the whiskers depict the range which includes 95% of the data, and the black dots are considered outliers. The solid line in the boxed area is the median and the dashed line is the mean. Using a Rank Sum Test, the mean value of the moss-treated pools demonstrate a statistically significant (p=0.04) lower level of THM's.

Figure 3:
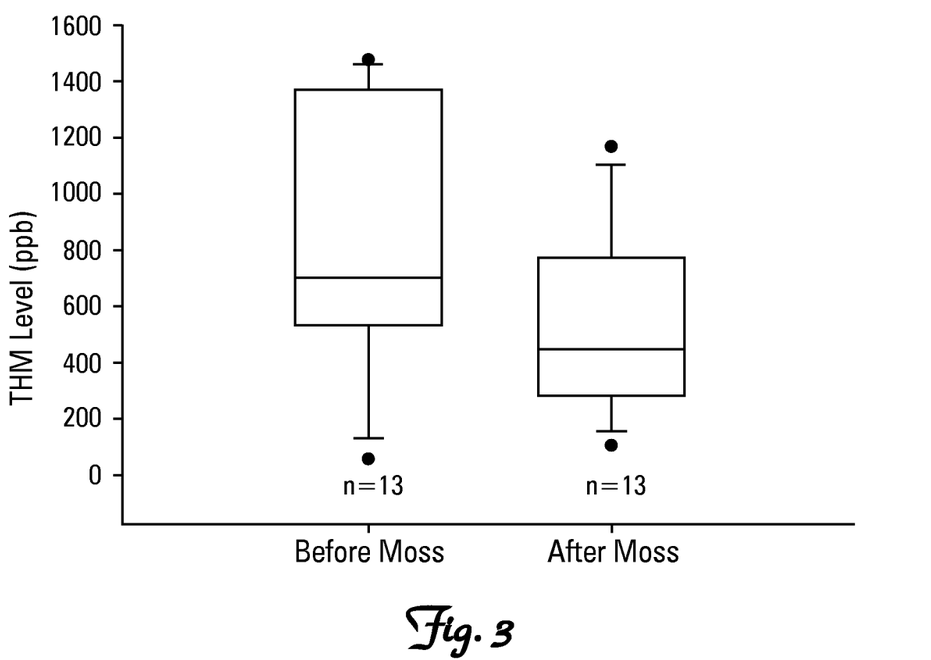
FIG. 3 shows the THM levels in thirteen swimming pools before and after treatment with the sphagnum moss system.

FIG. 3 is another box plot analysis of THM data from thirteen swimming pools where THM levels were determined prior to the addition of moss and again two months after moss treatment. The water in the moss-treated swimming pools was contacted with moss as described in the Materials and Methods for the leisure pool. However, the amount of moss varied from 6.5 grams/1000 gallons to 13 grams/1000 gallons based on pool temperature and the number of people using the pool. Water samples were collected and analyzed for THM levels as described in the Materials and Methods. The box plot parameters are the same as described above. Using a Student's Paired t-test, the moss-treatment demonstrates a significant decrease in THM with p=0.017.

Materials and Methods

The sphagnum moss system consists of sphagnum moss (*Sphagnum cristatum*) in strip or brick form and a contact chamber. The lap pool (approximately 75,000 gallons) had the moss in a CC-75 contact chamber, which is a plastic cylindrical container with a volume of approximately five gallons (available from Creative Water Solutions, Plymouth, Minn.). The contact chamber contained forty-nine 3.5 g strips (228 mm×30 mm×2-3 mm) and forty-nine 6.5 g strips (350 mm×30 mm×2-3 mm) of *Sphagnum cristatum* (490 grams total) arranged vertically on the bottom of the chamber. The strips were obtained from Coastpak Holdings, Ltd., Hokitika, New Zealand. All strips were individually contained in nylon mesh. Water taken from the main lap pool system was passed through the contact chamber at approximately 8 gallons per minute and fed back into the pool system. The leisure pool (approximately 86,000 gallons) had the moss placed into the pool surge tank using a STL contact chamber, which is a coated wire mesh crate with dimensions of approximately 3 feet by 18 inches by 12 inches (available from Creative Water Solutions, Plymouth, Minn.). The contact chamber contained 6 nylon mesh bags with 3 bricks (approximately 50 g/brick) of *Sphagnum cristatum* each and 2 nylon mesh bags with 2 bricks each (1,100 grams total). The STL contact chamber has four levels and two bags are put on each level. The bricks were obtained from Coastpak Holdings, Ltd., Hokitika, New Zealand and have dimensions of 20 cm×12 cm×0.6-0.7 cm. The surge tank is part of the pool system with constant flow-through. The sphagnum moss in each pool was replaced monthly.

The levels of THM in the water of the pools was measured using the methods described in two publications by the Hach Company, Loveland, Colo., U.S.A.: (1) Toba Lord, "Determination of Trihalomethanes (THMs), Trihaloacetic Acids (THAAs), and Other Disinfection By-Products (DBPs) in Drinking Water," and (2) DR/4000 Procedure, Method 10132, Trihalomethanes, THM PLUS Water Bath Method (2003), both of which are hereby incorporated by reference herein. A Hach spectrometer was not used; a Beckman DU-7400 spectrophotometer (available from Beckman Coulter, Inc., Brea, Calif., USA) was used instead.

The THM PLUS method reacts with the trihalogenated disinfection by-products formed by the disinfection of water with chlorine disinfectant in the presence of naturally occurring organic materials. The predominant DBP's formed are the trihalomethanes (THM): chloroform ($CHCl_3$), bromoform ($CHBr_3$), dichlorobromomethane ($CHCl_2Br$), and dibromochloromethane ($CHBr_2Cl$). These four compounds make up the Total Trihalomethanes (TTHM) group which is regulated under the Safe Drinking Water Act. The combined concentration of the TTHMs, reported as chloroform, is regulated to be 100 ppb or less.

In addition to the four trihalomethanes, seven other DBP's also react in the THM PLUS method. These other DBP's that react are: 1,1,1-trichloro-2-propanone, 1,1,1-trichloroacetonitrile, chloral hydrate, dibromochloroacetic acid, dichlorobromoacetic acid, tribromoacetic acid, and trichloroacetic acid. The THM PLUS method measures the four trihalomethanes and the seven other DBP's that react in the method (the eleven reactive compounds). These eleven reactive compounds present in a sample react with N,N-diethylnicotinamide under heated alkaline conditions to form a dialdehyde intermediate. The sample is then cooled and acidified to pH 2.5. The dialdehyde intermediate formed is then reacted with 7-napthylamine-1,3 disulfonic acid to form a colored Schiff base which absorbs at 515 nm. The color formed is directly proportional to the amount of the eleven reactive compounds present in the sample. The results are reported as ppb chloroform.

Water samples from the swimming pools were collected, at various times over the test period, in precleaned and certified 40 ml, amber vials (borosilicate) with air tight caps (Cat. #0040-0420-PC, Environmental Sampling Supply, Oakland, Calif.). Water was collected by submersing the vials under the water and capping them while submerged to eliminate any air in the sample. Water samples were stored at 0-4 degrees C. and run in the THM assay within 48 hours. Other appropriate methods of measuring THM can also be used.

The levels of the VOC's were measured by gas chromatography/mass spectrometry according to the EPA Compendium Method TO-15 (Determination Of Volatile Organic Compounds (VOCs) In Air Collected In Specially-Prepared Canisters And Analyzed By Gas Chromatography/Mass Spectrometry (GC/MS), Center for Environmental Research Information, Office of Research and Development, U.S. Environmental Protection Agency, Cincinnati, Ohio 45268, January 1999), the contents of which are hereby incorporated herein by reference. Analysis was performed by a certified laboratory (ALS Laboratory Group, Salt Lake City, Utah). Air samples were taken at three separate locations within the pool facility. Baseline samples were obtained twice, approximately one week apart, prior to addition of the sphagnum moss system. Air samples were taken again at the same three locations in the pool facility 28 weeks following installation of the sphagnum moss system. Air samples were obtained using certified and cleaned SUMMA vacuum canisters supplied by the ALS Laboratory Group using one SUMMA canister per location in the pool facility. A SUMMA canister is the air sampling industry term for a stainless steel "summa" polished (i.e., electropolished) passivated vessel used to collect a whole air sample. The SUMMA canisters were preset to fill with the air samples over approximately a four hour period. Following sample collection, the SUMMA canisters were shipped immediately to the ALS Laboratory Group for analysis. Other appropriate methods for measuring VOC's may also be used.

The above description and the drawing are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A method of reducing disinfection by-products in water treated with disinfectants comprising contacting the water with an amount of a non-decomposed moss effective to reduce the level of disinfection by-products, wherein the disinfection by-products whose level is reduced comprise one or more of the group of trihalomethanes and haloacetic acids.

2. The method of claim 1, wherein the water has been treated with a disinfectant selected from the group consisting of chlorinated, brominated, or other halogen containing disinfectants.

3. The method of claim 2, wherein the disinfectant is a disinfectant that includes chlorine.

4. The method of claim 1, wherein the non-decomposed moss is in the form of leaves or parts of leaves.

5. The method of claim 4, wherein the non-decomposed moss is in the form of compressed leaves or parts of leaves.

6. The method of claim 1, wherein the non-decomposed moss is placed in a carrier.

7. The method of claim 6, wherein the carrier is a mesh bag.

8. The method of claim 1, wherein the non-decomposed moss is placed in a contact chamber.

9. The method of claim 1, wherein the non-decomposed moss is placed in a filter cartridge housing.

10. The method of claim 1, wherein the non-decomposed moss is placed in a surge tank of a pool.

11. The method of claim 1, wherein the water is water in a spa, swimming pool, or splash deck.

12. The method of claim 1, wherein the level of disinfection by-products in the water is reduced by 20 percent or more after eight weeks.

13. The method of claim 1, wherein the level of disinfection by-products in the water is reduced by 40 percent or more after eight weeks.

14. The method of claim 1, wherein the level of disinfection by-products in the water is reduced by 60 percent or more after eight weeks.

15. The method of claim 1, wherein the disinfection by-products whose level is reduced comprise chloroform.

16. The method of claim 1, wherein the disinfection by-products whose level is reduced comprise one or more of chloroform, bromoform, dichlorobromomethane, and dibromochloromethane.

17. The method of claim 1, wherein the non-decomposed moss is selected from the group consisting of *sphagnum papillosum, sphagnum cristatum*, and mixtures thereof.

18. The method of claim 1, wherein the level of disinfection by-products is reduced in the air above the water.

19. The method of claim 18, wherein the disinfection by-products whose level is reduced in the air above the water comprise one or more of chloroform, bromoform, dichlorobromomethane, and dibromochloromethane.

20. The method of claim 18, wherein the disinfection by-product whose level is reduced in the air above the water is chloroform.

21. The method of claim 18, wherein the level of disinfection by-products in the air above the water is reduced by 20 percent or more after 28 weeks.

22. The method of claim 18, wherein the level of disinfection by-products in the air above the water is reduced by 40 percent or more after 28 weeks.

23. The method of claim 1, wherein the disinfection by-products whose level is reduced comprise one or more trihalomethanes.

24. The method of claim 1, wherein the disinfection by-products whose level is reduced comprise one or more haloacetic acids.

25. A method of reducing disinfection by-products in water treated with disinfectants comprising contacting the water with an amount of a non-decomposed moss effective to reduce the level of disinfection by-products, wherein the disinfection by-products whose level is reduced comprise one or more of chloroform, bromoform, dichlorobromomethane, dibromochloromethane, 1,1,1-trichloro-2-propanone, 1,1,1-trichloroacetonitrile, chloral hydrate, dibromochloroacetic acid, dichlorobromoacetic acid, tribromoacetic acid, and trichloroacetic acid.

26. A method of reducing disinfection by-products in water treated with disinfectants comprising contacting the water with an amount of a non-decomposed moss effective to reduce the level of disinfection by-products, wherein the disinfection by-products whose level is reduced consist of the group of chloroform, bromoform, dichlorobromomethane, dibromochloromethane, 1,1,1-trichloro-2-propanone, 1,1,1-trichloroacetonitrile, chloral hydrate, dibromochloroacetic acid, dichlorobromoacetic acid, tribromoacetic acid, and trichloroacetic acid.

27. A method of reducing disinfection by-products in water treated with disinfectants comprising contacting the water with an amount of a non-decomposed moss effective to reduce the level of disinfection by-products, wherein the disinfection by-products whose level is reduced consist of the group of chloroform, bromoform, dichlorobromomethane, and dibromochloromethane.

\* \* \* \* \*